United States Patent [19]

Sawyer, Jr.

[11] 4,116,826
[45] Sep. 26, 1978

[54] WATER PURIFICATION METHODS

[75] Inventor: Edgar W. Sawyer, Jr., Hagerstown, Md.

[73] Assignee: International Telephone and Telegraph Corp., Nutley, N.J.

[21] Appl. No.: 806,202

[22] Filed: Jun. 13, 1977

Related U.S. Application Data

[62] Division of Ser. No. 636,263, Nov. 28, 1975, Pat. No. 4,054,515.

[51] Int. Cl.² ............................................. C02B 1/14
[52] U.S. Cl. .................................... 210/27; 210/28; 210/29; 210/40
[58] Field of Search .......................... 210/24, 27-29, 210/36, 40, 50-53, 59, 64, 73 R, 80, 170

[56] References Cited

U.S. PATENT DOCUMENTS

| | | | |
|---|---|---|---|
| 2,808,154 | 10/1957 | Scott | 210/29 |
| 3,171,801 | 3/1965 | Rice et al. | 210/80 |
| 3,873,581 | 3/1975 | Fitzpatrick et al. | 210/24 |
| 3,917,530 | 11/1975 | Boske | 210/170 |
| 3,959,128 | 5/1976 | Harris | 210/24 |

OTHER PUBLICATIONS

Robertson, R.H.S., "Sepiolite: A Versatile Raw Material" in Chemistry and Industry, Nov. 1975, pp. 1492-1495.

Primary Examiner—Charles N. Hart
Assistant Examiner—Ivars Cintins
Attorney, Agent, or Firm—John T. O'Halloran; Peter C. Van Der Sluys

[57] ABSTRACT

Treating water with various grades of attapulgite clay and sepiolite using contacting or percolation techniques removes substances not removable by standard water purification methods under many conditions. Substances such as pesticides, toxins, hormones, heavy metal cations and viruses are removed from water by adsorption upon the clay surface. When contacting is employed, the clay containing the adsorbed substances is subsequently removed by sedimentation or filtration. The clays can be regenerated by appropriate chemical or thermal techniques.

14 Claims, 3 Drawing Figures

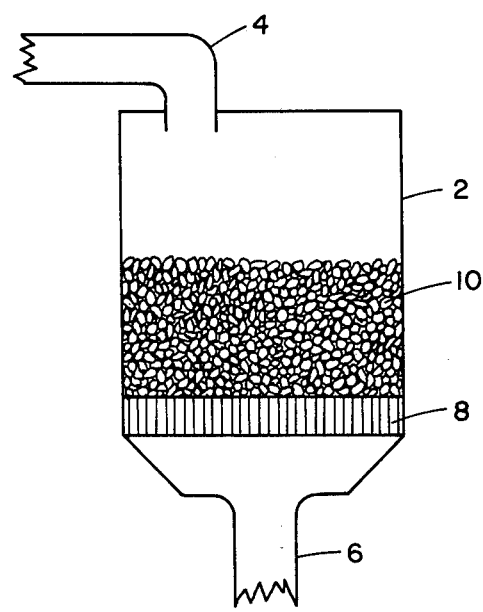
Fig. 1
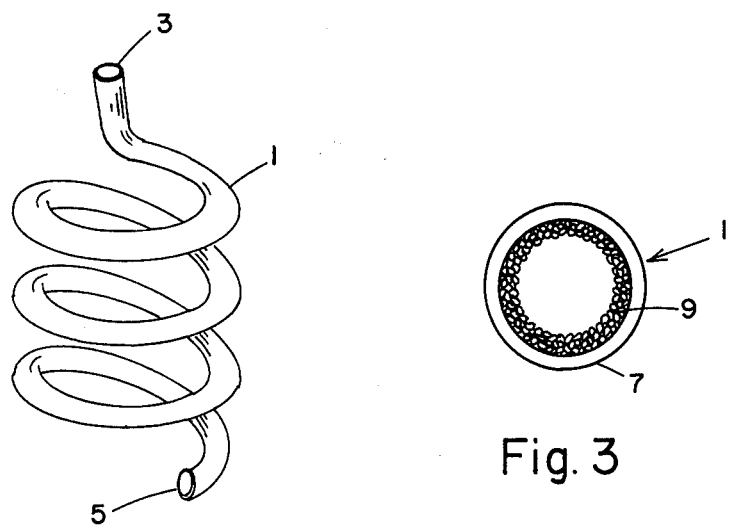
Fig. 2
Fig. 3

WATER PURIFICATION METHODS

This is a division, of application Ser. No. 636,263, filed Nov. 28, 1975, now U.S. Pat. No. 4,054,515.

BACKGROUND OF THE INVENTION

The shortage of pure drinking water is rapidly becoming a serious problem. Currently available methods for purifying water from natural and reclaimed sources are generally incapable of removing certain chemicals and biologically active substances that are appearing in water supplies in alarmingly increasing proportions. It appears that biologically active substances that are intentionally or accidentally dumped into our ponds, streams and rivers or enter ground strata via septic systems could become potentially dangerous substances when the water from these sources is treated by conventional means and is eventually used for drinking.

Standard methods for purifying water such as coagulation, sedimentation, filtration and chemical treatment are effective for removing most contaminants and for killing most of the microorganisms present. These methods, however, are not completely effective for removing substances such as hormones, pesticides, viruses, toxins and heavy metal cations. The use of female steroids for birth control purposes, for example, and growth hormones for fattening-up beef and poultry, has resulted in significant quantities of these hormones finding their way into municipal water supplies, particularly in large metropolitan areas.

Methods for the treatment of sewage, such as removal of solids by flocculation followed by sedimentation and centrifuging, and removal of bacteria by chemical treatment are generally ineffective for removing hormones and viruses. When the "harmless" liquid effluents from sewage treatment plants are dumped into inland waters these hormones are still present in the water. When inland waters are subsequently used as backups for water reservoirs and other storage facilities for municipal water supplies, these intractable contaminants end up in water that is used for drinking purposes. Subsequent purification procedures are generally incapable of removing these hormones so that it is possible for them to enter the human body along with the drinking water. The same problem, in more or less increasing proportions, is true for other substances such as viruses, toxins, heavy metal cations and pesticide residues.

Another potential source contributing to the human self-contamination cycle is the backyard swimming pool. Viruses, toxins and hormones which are deposited in these backyard pools gradually increase in concentration since they are generally immune to the effects of routine filtering and chemical treatment. When the pools are eventually emptied these biologically active substances could conceivably reach the bathroom and kitchen water taps. This is particularly true for large inland municipalities where the effluents from sewerage treatment plants cannot be discharged directly into the sea from which the possibility of return is extremely remote.

The purpose of this invention, therefore, is to provide methods and materials for removing potentially harmful substances which are generally immune to standard sewage treatment and water purification processes from waste streams and/or potable water.

SUMMARY OF THE INVENTION

Treating water with certain minerals removes substances which do not respond to other methods of water purification. One embodiment comprises the use of attapulgite clay powder in combination with alum for treating potable water. A further embodiment comprises the method of percolating water through a column containing granular attapulgite clay subsequent to standard purification treatments or prior thereto.

BRIEF DESCRIPTION OF THE DRAWINGS

FIG. 1 is a side sectional view of a percolation chamber according to this invention;

FIG. 2 is a front perspective view of an alternate embodiment of the device of FIG. 1; and FIG. 3 is a cross-sectional view of the embodiment of FIG. 2.

DESCRIPTION OF THE PREFERRED EMBODIMENT

In order to determine the adsorptivity of clay materials for various type viruses the following series of tests were performed.

Since the adsorption properties of clay are a known function of the available surface and surface characteristics of the clay resulting from the thermal treatment of the clay and the particle size, the clay was classified according to fineness of grind and thermal treatment. In order to determine virus adsorption over a wide range of sizes, a relatively small virus and a relatively large size virus were employed. Attapulgite clay products, consisting of magnesium aluminum silicate, and commercially available from the Floridin Co., Berkeley Springs, W. Va., were used as typical examples of commercially available and feasible products for the purpose of this invention. The attapulgite clay having an average particle size of approximately $26\mu$ was used as a fine grade clay for comparison to a clay having a mean particle size of approximately $45\mu$ as a coarse grade clay.

Certain high-sorbency, high-surface-area clay minerals—namely, attapulgite, sepiolite, and other minerals similar to attapulgite that are classified roughly as palygorskites, that are commercially available at economical prices and where large worldwide reserves exist—were considered to be of prime interest for evaluation in this invention. With these minerals the adsorption of ions, larger molecules and materials of colloidal size occurs on the outer surfaces of the needle structure and surfaces resulting from cleavage where availability of these surfaces is limited in access by the pore sizes of larger particles resulting from needle agglomeration. Consequently, the adsorptivity they exhibit is strongly dependent on their processing.

Clays used in this study and their processing are described below:

HVM — high volatile matter. This type has been dried at low temperatures, has the highest BET (Brunauer, Emmett, Teller) surface area and surface available for adsorption and is capable of slaking in water. Thus, in water systems this grade can only be used in contacting studies.

RVM — regular volatile matter. RVM clays have been semi-calcined at higher temperatures (approximately 500° F.) than HVM clays. They exhibit about half the BET surface area of the HVM clays, but only slightly less available surface. They still are slakeable to some extent but not entirely. Therefore, RVM products can only be used in contacting studies. Because a certain percentage of the clay is nonslaking, porosity of agglomerates becomes of importance with this grade and has an effect on adsorption of colloidal particles—small pores will not admit large particles and thus available surface is decreased.

LVM — low volatile matter. LVM clays are calcined at higher temperatures (approximately 1000° F.) which result in particle sintering. Particles do not slake in water and this grade is the only one of the three suitable for percolation studies in aqueous systems. Because of sintering (and possibly structure collapse) LVM clays exhibit the lowest available surface and a much smaller pore size distribution and total pore volume than the RVM clays. The reduced availability of pore surface is reflected in very poor adsorption of colloidal particles particularly in granular grades. Grinding LVM granulars into fine powders increases the available surface to a major extent. Consequently, when considering adsorptive surface available for molecular contaminants in water HVM>RVM>LVM. For molecular agglomerates and colloids HVM>RVM>>>LVM and powdered LVM>>granular LVM.

The clays and minerals used in the following examples are descibed below in tabular form.

For the materials listed, the free moisture (FM) was determined by drying the material to a constant weight at 220° F. and the dry particle size was determined by using an Alpine classifier. The attapulgite products are commercial products available from the Floridin Co., as described earlier. The sepiolite material, designated X-1000, is a commercially available clay product from the Industrial Mineral Ventures Co., Golden, Colo. The amorphous zeolite is a fine particle size synthesized sodium aluminum silicate available from the J. M. Huber Corp., Havre de Graze, Md.

| Designation | Compositon | % Free Moisture | Dry Particle Size % +44u |
|---|---|---|---|
| Fine Ground HVM | Colloidal Attapulgite | 14.2 | 1.4 |
| Coarse Ground HVM | Colloidal Attapulgite | 15.0 | 84.2 |
| Fine Ground RVM | Semi-calcined Attapulgite | 5.0 | 1.1 |
| Coarse Ground RVM | Semi-calcined Attapulgite | 7.5 | 13.2 |
| Fine Ground LVM | Calcined Attapulgite | 0.5 | 0.18 |
| Coarse Ground LVM | Calcined Attapulgite | 0.2 | 1.8 |
| 30/60 LVM | Granulated, Calcined Attapulgite | 0.1 | 95% through a 30 mesh screen and on a 60 mesh screen |
| Sepiolite X-1000 | Colloidal Sepiolite | 12.2 | 0.15 |
| Amorphous Zeolite | Sodium Aluminum Silicate (an amorphous zeolite) | 6.0 | — |

In these studies contacting consists of adding powdered clay to contaminated water, stirring for a specified period of time at a specified temperature and filtering to remove the clay plus adsorbed material. This technique can be practiced using powdered HVM, RVM and LVM grades. Percolation consists of passing the contaminated water through a column packed with granular LVM grades at a prescribed throughput rate until the sorptive capacity of the column is exhausted. The capacity of the column is inversely proportional to the rates used—higher rates result in lower capacities. In distinction from mechanical filtration the capacity is much lower for larger contaminating particles (colloids and molecular agglomerates) than it is for molecular contaminants.

Two types of viruses were used in this study to exemplify the range of possibilities available in clay surface-virus adsorption interactions in aqueous media. Polio virus, Type I, is a small ($\sim 20$ m$\mu$) virus with a RNA (ribonucleic acid) core; Herpes simplex is a larger ($\sim 200$ m$\mu$) virus with a DNA (deoxyribonucleic acid) core.

EXAMPLE 1

ADSORPTION OF HERPES SIMPLEX VIRUS TYPE W1-38 ($10^{4.8}$/ml CONCENTRATION)

| | Unadsorbed Viruses (as $TCID_{50}$) | |
|---|---|---|
| Type of Attapulgite Clay | Fine Grade | Coarse Grade |
| High Volatile Matter | $<10^{0.0}$/ml | $<10^{0.0}$/ml |
| Regular Volatile Matter | $<10^{0.0}$/ml | $<10^{0.0}$/ml |
| Low Volatile Matter | $<10^{0.0}$/ml | $<10^{0.0}$/ml |
| Sand (Control) | $10^{4.8}$/ml | — |

Example 1 shows the adsorption of Herpes simplex virus designated as type W1-38, supplied by the Wisconsin Alumni Research Foundation, as a typical virus having a relatively large molecular size of 0.2$\mu$. Both DNA and RNA core organisms were used throughout the range of clay materials evaluated for adsorption. In order to determine the adsorptivity of two different grades of clay and for the three types of volatile matter content, the virus was made to contact the various types of clay in a wet suspension. After contacting the various type clays for 2 minutes, the liquid containing the virus was then filtered and a determination was made on the amount of virus remaining in the liquid.

The method used in determining the concentration of virus remaining in the liquid after contacting the clay is the indirect method of measuring the effect of damage on live human tissue. The virus was prepared by melting vials of frozen Herpes simplex virus materials and centrifuging 1500 grams of the material for 10 minutes to remove any tissue debris. 12 ml of virus material were added to a bottle containing 120 ml of sterile distilled water.

The virus adsorption studies were carried out using the following test procedure: 6 ml of virus culture material was added to a sterile bottle containing 60 ml of sterile distilled water. Aliquots (18 ml) of the diluted viral suspension were placed in a sterile 50 ml plastic centrifuge tube containing 2 g of sterile adsorbent. The inoculated tube was thoroughly mixed by shaking for 1 minute and immediately filtered through a sterile plastic filter unit containing a 0.45 micron Nalgene membrane. The filtrates were titrated for virus infectivity in HEp II cell system using a microscopic examination to determine cytopathic effects. Virus counts are given as $TCID_{50}$ (tissue culture infectious dose with a 50% response). The titration (or specific dilution sequence) technique used is described in "Methods for the Examination of Poultry Biologics," Chapter 2, National Research Council Publication 1038, National Academy of Science (1971) and in many standard textbooks on virology. Clay concentrations were varied where desired. Ground sand was run as a control so that virus adsorption is reflected by the difference in titratable activity between any particular clay and the control.

For the various grades of clay utilized the test shown in Example 1, the adsorption properties for the high, regular and low volatile matter for the Herpes simplex virus tested was equivalent for both the fine and the coarse grades of clay. The TCID remaining in solution for the sand control was $10^{4.8}$/ml, which is equal to the concentration of virus in the liquid solution before contacting. This shows that the various grades of attapulgite clay are, therefore, effective in removing all the Herpes simplex virus from solution whereas sand is completely ineffective.

weight clay per weight of virus-containing liquid. Example 3 shows that for a $10^{6.6}$/ml polio virus concentration, 10% fine grade attapulgite clay in suspension is sufficient for removing substantial quantities of polio virus from the liquid. Although attapulgite clay containing the three classes of volatile matter listed is effective for removing polio virus in different degrees depending upon the concentration of the various clays in suspension, the high volatile matter is the most efficient adsorber for polio virus at all concentrations tested.

The examples shown above are indicative of the capability of the various types of colloidal grade clay for effectively removing both relatively large particle diameter Herpes simplex type viruses and relatively small particle diameter polio type viruses from water. The phenomena that cause adsorption are not well understood at this time but are postulated to be related to such surfaces characteristics as the surface structure and available surface of the clay along with the effective positive charge that these viruses assume, and the negative charge that the clays assume in a water solution. The volatile content as expressed by the designation of low, regular and high volatile matter is also indicative as to the degree of disintegration that the various clays encounter upon contact with water, and the amount of surface available after the sintering effect of heating. The disintegration process is briefly described as the disassociation of the individual clay particles into acicular type needles having a 0.01μ diameter and a length of 1μ. The combination of the electrical attraction of the clay for cationic substances, such as viruses, and the ultrafine geometry of the clay needles in suspension partially accounts for the very effective adsorption properties of the clay substances involved. The high volatile matter attapulgite clay readily disintegrates, as described above, whereas the regular volatile and low volatile matter disintegrate to lesser degrees, respectively.

The use of fine clay powders for removing polio and Herpes type viruses is suitable for both municipal and home type water supplies. This is particularly important when such water supplies become accidentally contaminated by negligent disposal of virus-contaminated substances or intentionally as in the event of germ warfare.

EXAMPLE 2.

ADSORPTION OF POLIO VIRUS TYPE I ($10^{7.2}$/ml CONCENTRATION)

| | Unadsorbed Viruses (as $TCID_{50}$) | | | |
|---|---|---|---|---|
| | 30 Minutes Contact Time | | 5 Minutes Contact Time | |
| Type of Adsorbent | Fine Grade | Coarse Grade | Fine Grade | Coarse Grade |
| High Volatile Matter Attapulgite | $<10^{0.0}$/ml | $<10^{0.0}$/ml | $10^{0.3}$/ml | $10^{0.3}$/ml |
| Regular Volatile Matter Attapulgite | $10^{1.0}$/ml | $10^{1.7}$/ml | $10^{0.7}$/ml | $10^{1.7}$/ml |
| Low Volatile Matter Attapulgite | $10^{1.4}$/ml | $10^{2.5}$/ml | $10^{1.3}$/ml | $10^{2.0}$/ml |
| Sand (Control) | $10^{7.2}$/ml | — | $10^{6.3}$/ml | — |
| High Volatile Matter Sepiolite | $<10^{0.0}$/ml | — | — | — |
| Zeolex 80 (an amorphous zeolite) | $10^{1.0}$/ml | — | — | — |

Example 2 shows the adsorption of polio type virus for various clay materials. The effect of contact time is also shown for contacting the virus-containing liquid with clay for 5 minutes and for 30 minutes. The polio virus type tested was Type I supplied by the Wisconsin Alumni Research Foundation. This virus was used as exemplary of a small molecular size virus having a 0.2μ molecular size. The virus solutions were prepared in a similar manner as for the Herpes simplex virus described above and the TCID determination using human tissue is the same as described earlier. The polio virus concentration for this test was $10^{7.2}$/ml. Example 2 shows that the attapulgite and sepiolite clays are effective for removing most of the polio virus from the liquid solution after a contact period of 30 minutes. For a contact period of 30 minutes the high volatile matter attapulgite clay showed 100% adsorption for both the fine and coarse grades compared to nearly 100% adsorption for both fine and coarse grades for a 5 minute contact period. Example 2, therefore, shows that the high volatile matter attapulgite clay is effective for removing substantially all traces of polio virus from a concentrated solution in a relatively short period of contact time. Zeolex 80, an amorphous or non-crystalline zeolite, which is an example of a zeolite, was found to be equivalent to the regular volatile matter attapulgite for polio virus adsorption for the same increment of contact time.

EXAMPLE 3.

ADSORPTION OF POLIO VIRUS TYPE I ($10^{6.6}$/ml CONCENTRATION)

| | | Unadsorbed Viruses (as $TCID_{50}$) | | |
|---|---|---|---|---|
| | % Absorbent | Regular Volatile Matter | Low Volatile Matter | High Volatile Matter |
| Fine Grade Attapulgite Clay | 1.25 | $10^{6.8}$/ml | — | — |
| Fine Grade Attapulgite Clay | 2.50 | $10^{3.6}$/ml | — | — |
| Fine Grade Attapulgite Clay | 5.00 | $10^{3.3}$/ml | $10^{2.6}$/ml | $10^{1.2}$/ml |
| Fine Grade Attapulgite Clay | 10.00 | $10^{1.8}$/ml | $10^{2.3}$/ml | $<10^{0.0}$/ml |
| Fine Grade Attapulgite Clay | 20.00 | $10^{1.3}$/ml | $10^{0.2}$/ml | $<10^{0.0}$/ml |
| Sand Control | 10.00 | $10^{7.6}$/ml | — | — |

In order to determine the effect of the quantity of clay on the adsorption of polio virus the amount of clay was varied from 1.25% to 20% for a fixed concentration of virus in solution. Examples 1 and 2 indicate the adsorption based on a clay concentration of 10% by The virus adsorbed upon the clay surface in all the examples listed was found to remain viable and it was also discovered that the adsorption process is irreversible. If, for example, the clay is used to adsorb virus from potable water supplies, the clay containing the virus should be removed so that the adsorbed virus could be destroyed by heat or chemicals.

The use of attapulgite clay powder in home swimming pools and aquariums for virus removal is also suggested in view of the good adsorptive properties of these clays for large and small virus molecules. In these applications the clay could be made to contact the virus by broadcasting in powder form over the surface of the swimming pool or aquarium, and removed by standard sedimentation and/or filtration techniques. The use of clay for cleaning virus from swimming pools by adsorption is an important application since the various infections and diseases transmitted by persons using these pools are known to be of viral origin.

The effect of clay powder as a means of adsorption of hormones from water is shown in Example 4. Although most hormones are insoluble in water, diethylstilbesterol was chosen as an intermediate size molecule to determine whether the good adsorption properties exhibited for viruses is also true for hormones. In this example two different concentrations of diethylstilbesterol (5 ppb and 50 ppb) were suspended in water and were allowed to contact two different concentrations of high volatile matter fine grade attapulgite clay. The amount of hormones remaining in suspension was determined by known hormone analytical techniques. For the 1.1% clay concentration the amount of DES adsorbed was 68% for 5 ppb compared to 60% for 50 ppb. 10% clay by weight of water containing 5 ppb DES adsorbed 76%, and adsorbed as much as 89% of the 50 ppb DES suspension. Example 4, therefore, shows that relatively small concentrations of clay are capable of removing substantial quantities of hormones from liquid suspensions.

EXAMPLE 4.

ADSORPTION OF DIETHYLSTILBESTEROL HORMONE

| Attapulgite Clay High Volatile Matter Fine Grade | Percent DES Adsorbed 5 ppb DES | 50 ppb DES |
|---|---|---|
| 1.1% | 68% | 68% |
| 10.0% | 76% | 89% |

Example 5 shows the effective adsorption of a phosphate insecticide by high volatile matter attapulgite clay. Equal volumes of distilled water were contaminated with 100 ppb diazinon insecticide. Diazinon was chosen as an example of one of the pesticides available in different parts of the world. 10% attapulgite clay high volatile matter was added in powder form to a volume of distilled water contaminated with 100 ppb diazinon. The clay suspension was then shaken lightly to promote good contact between the clay surface and the liquid and subsequently poured through a fine grade micropore filter. The filtrate was then measured for concentration of diazinon remaining in the solution by standard insecticide determination analysis. The amount of diazinon remaining in the filtrate after contact with the clay was 15%. An equal volume of sand was added to an equivalent volume of diazinon-contaminated distilled water and subjected to the same filtration and analysis as for the clay. The amount of diazinon remaining in the filtrate from the liquid in contact with the sand was 57.5%. This shows that attapulgite clay is very effective for removing traces of this insecticide from water and may find possible aplication as an internally administered antidote for treatment of insecticide poisoning as well as for removing insecticides from potable water supplies.

EXAMPLE 5.

ADSORPTION OF DIAZINON INSECTICIDE (100 ppb DOSAGE)

| 10% Adsorbent | Percent Diazinon Remaining In Solution |
|---|---|
| High Volatile Matter Fine Grade | 15.0% |
| Sand Control | 57.5% |

In order to determine the effect of clay for removing cadmium ions from contaminated water supplies, the following tests were performed.

1% and 10% concentrations of fine ground HVM attapulgite clay were added to water contaminated with cadmium. Since the adsorption of various ions is known to be dependent upon the pH of the liquid medium, the adsorption studies were made at both a pH value of 6 and a pH value of 10. Samples were prepared using distilled water to which 1 ppm concentration of salts were added. After contacting the contaminated water with the various concentrations of clay and the 10% sand control, the contaminated liquids were filtered and the filtrates were analyzed for cadmium ion content by standard methods of quantitative analysis. For all the samples tested it was found that both the 1% and 10% clay concentrations were very effective for removing cadmium ions from solution. Examples 6 indicates the possible use of attapulgite clay as an antidote for the ingestion of poisonous cadmium salts as well as for removing the ion from the contaminated water supplies.

EXAMPLE 6.

ADSORPTION OF CADMIUM IONS (1 ppm CONCENTRATION)

| Fine Attapulgite Clay High Volatile Matter | ppm Remaining In Solution Cadmium pH 6.0 | 10.0 |
|---|---|---|
| 1% | 0.04 | 0.14 |
| 10% | < 0.03 | 0.04 |
| Sand Controls | 0.78 | 0.72 |

In order to determine the effect of clay on removing mycotoxins from water, the following tests were performed and the results are shown in Examples 7.

EXAMPLE 7

ADSORPTION OF AFLAVOTOXINS

| High Volatile Matter Fine Attapulqite Clay | % Aflavotoxin Adsorbed 0.5 ppb Concentration | 5.0 ppb Concentration |
|---|---|---|
| 1.0% | 100.0% | >97.5% |
| 10.0% | 100.0% | 100.0% |

Since find grade high volatile matter attapulgite clay has been shown to be an effective contact adsorbent for all materials tested, this material was used at 1.0% and 10% concentrations in order to remove mycotoxins from water. Aflavotoxins were selected as characteristic of a large group of mycotoxins which could be found in contaminated water supplies particularly if drainage from mold infested agricultural products enters the water supplies. The aflavotoxins were added to distilled water in concentrations of 0.5 ppb and 5 ppb, respectively. For the 1.0% concentration of clay added to the 0.5 ppb concentration it was found that 100% of the aflavotoxins were adsorbed and for the 5 ppb concentration greater than 97% were adsorbed. For the 10% clay added to both the 0.5 ppb contaminated water and the 5.0 ppb contaminated water, the amount of aflavotoxins adsorbed was 100%. The mycotoxin content was determined by standard methods of analysis. Example 7 indicates, therefore, that fine grade high volatile matter attapulgite clay is very effective for removing mycotoxin contaminants from water using contact adsorption.

The efficient decontamination of potable water by contact adsorption has been shown by the use of various grade clays and suggests application for ecological improvement of inland surface and well waters by relatively inexpensive clay treatment. The use of fine grade high volatile matter attapulgite is effective for removing impurities from water supplies, swimming pools, aquariums, and for the treatment of home and municipal fluid waste materials. The method suggests contacting the clay material with the contaminated water by either broadcasting an effective quantity of powder over the surface of the water or by passing the contaminated water through a bed containing the clay particles deposited upon an inert filter substance.

While the contacting technique for water purification is feasible in many existing sewage treatment and municipal water supply treatment plants, there are many possible situations where percolation treatment would be more desirable and/or advantageous. Percolation is defined for the purpose of this invention as the passing of the contaminated water through a column packed with granular adsorbent. Columns are generally vertical and directional flow either with or against the force of gravity can be employed.

When this method is practiced only the granular LVM (calcined) grades of clay can be utilized. The LVM grades are necessary because they are the only ones that will maintain their shape without disintegrating in water; granular grades are specified because inter-granular passages must exist to allow a free path for the water to pass through the column. Amounts of adsorption occurring or capacity in percolation are generally anticipated to show some sort of inverse relationship to the throughput rate and the size of the material being adsorbed — e.g. (1) high percolation rates will show lower column capacities than low percolation rates and (2) larger particle size water contaminants such as viruses will show much lower adsorbency than molecular-sized or ionic contaminants because of the differences in surface available to each.

To demonstrate the utilization of this invention for contaminant removal using the percolation technique, runs were tried with water containing diazinon, aflatoxin $B_1$ and diethylstilbesterol. The percolation column used consisted of a Chromoflex column, K4203020, size 256 (int. diam. 1.7 inches) with a sintered glass disk at its base plus a teflon needle-valve to control flow. A 30/60 mesh attapulgite granular LVM clay was used to pack the column. A 300 g portion filled the column to a height of ~15 inches. Prior to these runs Methylene blue chloride experiments were carried out at the proposed throughput rates to determined that these column dimensions were adequate to prevent bypass and channeling.

As a first step in the evaluations to determine column capacities for contaminants, the columns were flushed with sterile water to wash out fines. Contaminated water was run in on top of the column before the final water was drained and this retained volume was subtracted from the final percolation volume. Rates used were 20 and 60 cc/minute (equivalent to 960 gallons/ton/hour and 2882 gallons/ton/hour). Effluent materials were checked without filtration using standard analytical techniques. Water samples evaluated for percolation adsorption were contaminated with: (1) 20 ppb of aflatoxin $B_1$ as an example of a mycotoxin and shown in Example 8; (2) 100 ppm diazinon as an example of a phosphate pesticide and shown in Example 9; and (3) 50 ppb of diethylstilbesterol as an example of a hormone and shown in Example 10.

EXAMPLE 8

PERCOLATION SORPTION OF 20 ppb AFLATOXIN $B_1$ SOLUTION BY 30/60 LVM ATTAPULGITE

| Percolation Time | Filtrate Evaluation for Aflatoxin $B_1$ |
|---|---|
| | 20 cc/minute flow rate |
| 1 hour | not detectable |
| 2 hours | not detectable |
| 4.25 hours | not detectable |
| | 60 cc/minute flow rate |
| 20 minutes | not detectable |
| 40 minutes | not detectable |
| 100 minutes | not detectable |

EXAMPLE 9.

PERCOLATION SORPTION OF 100 ppb DIAZINON SOLUTION BY 30/60 LVM ATTAPULGITE

| Percolation Time | Filtrate Evaluation for Diazinon |
|---|---|
| | 20 cc/minute flow rate |
| 1 hour | not detectable |
| 2 hours | not detectable |
| 4.25 hours | 45 ppb |
| | 60 cc/minute flow rate |
| 20 minutes | not detectable |
| 40 minutes | 10 ppb |
| 100 minutes | 65 ppb |

EXAMPLE 10.

PERCOLATION SORPTION OF 50 ppb DIETHYLSTILBESTEROL SOLUTION BY 30/60 LVM ATTAPULGITE

| Percolation Time | Filtrate Evaluation for DES |
|---|---|
| | 20 cc/minute flow rate |
| 1 hour | 0 ppb |
| 2 hours | 0 ppb |
| 4.25 hours | 0 ppb |
| | 60 cc/minute flow rate |
| 20 minutes | 0 ppb |
| 40 minutes | 1 ppb |
| 100 minutes | 2 ppb |

Translating these results into gallons per ton capacity of the clay for contaminants, they are summarized in Example 11.

EXAMPLE 11.

CAPACITIES OF 30/60 LVM ATTAPULGITE FOR WATER CONTAMINANTS

| Contaminant | Percolation Rate (gals./ton/hr.) | Time (hrs.) | Column Capacity (gals./ton) |
|---|---|---|---|
| 20 ppb Aflatoxin | 960 | 4.25 | >4100 |
| | 2882 | 1.67 | >4800 |
| 100 ppb Diazinon | 960 | 2.0 | Between 1920 & 4100 |
| | 2882 | 0.33 | Between 961 & 1921 |
| 50 ppb Diethylstil- | 960 | 4.25 | >4100 |
| | 2882 | 0.33 | Between |

EXAMPLE 11.-continued

CAPACITIES OF 30/60 LVM ATTAPULGITE FOR WATER CONTAMINANTS

| Contaminant | Percolation Rate (gals./ton/hr.) | Time (hrs.) | Column Capacity (gals./ton) |
|---|---|---|---|
| besterol | | | 960 & 1921 |

Another example of the use of the percolation technique to improve the potability of contaminated water is shown in Example 12 for water solutions of the heavy metal cations arsenic, cadmium, lead and mercury. Each cation was dissolved in an acid solution at about 1.00 ppm. The percolation column was as described above using 30/60 LVM attapulgite. Throughput rates were 20 cc/minute and 60 cc/minute. Column effluents were not filtered but were examined for each contaminating ion by standard methods of quantitative analysis.

EXAMPLE 12.

PERCOLATION ADSORPTION OF HEAVY METAL CATIONS

| Percolation Rate at Times Shown | Effluent Concentrations in ppm | | | |
|---|---|---|---|---|
| | Arsenic | Cadmium | Lead | Mercury |
| 20 cc/min. | | | | |
| 1 hr. | 0.02 | <0.01 | <0.01 | 0.004 |
| 2 hrs. | 0.12 | <0.01 | <0.01 | 0.016 |
| 4.5 hrs. | 0.56 | <0.01 | <0.01 | 0.116 |
| Original Conc. | 0.97 | 1.00 | 1.07 | 1.11 |
| 60 cc/min. | | | | |
| 20 min. | 0.33 | <0.01 | <0.01 | 0.010 |
| 40 min. | 0.16 | <0.01 | <0.01 | 0.072 |
| 100 min. | 0.68 | <0.01 | <0.01 | 0.152 |
| Original Conc. | 1.02 | 1.00 | 1.07 | 1.11 |

These data illustrate the efficient sorptivity of the granular LVM attapulgite for cadmium, lead and mercury and the fairly good capacity of the clay for arsenic.

As previously indicated, the column efficiency was better at the lower rate. This is obvious when the sorptivity for mercury and arsenic is compared at equal throughput volumes (20 cc/min. at 2 hours and 60 cc/minute at 40 minutes).

Outside of standard methods of treating municipal and industrial water supplies such as broadcasting the clay powder along with alum followed by sedimentation and filtration the rapid adsorptive properties for the clay samples tested suggested the following home-type applications.

FIG. 1 shows a metal or plastic container 2 having an inlet 4 and outlet 6. A fine grade filter 8 can also be inserted within the container 2 to prevent materials from passing through the outlet 6. Particulate clay material 10 is enclosed within the container 2 between the inlet 4 and outlet 6. Incoming water through inlet 4 would then transport by percolating through the clay material 10 where adsorption would occur. The treated water would then pass out the outlet 6. The granular clay material 10 could be periodically removed and replaced in order to provide continuously active surfaces for adsorption. If desired other adsorbing materials such as charcoal and sand could be used in combination with the clay material.

FIG. 2 shows another embodiment for providing contact between the granular clay adsorbent and the water to be treated. A coiled tubing 1 having an inlet 3 at one end and an outlet 5 at another end contains a coating of clay material on the inner surface of the tubing. By adjusting the tubing diameter, the number of coil turns and the water flow rate, the water could be made to effectively wet the clay for efficient contact and adsorption.

FIG. 3 shows a cross-section of the tube 1 having a tube wall 7 containing a coating of particulate clay material 9. The tubing 1 could be replaced after the clay material 9 is no longer capable of adsorption, or the clay material 9 could be dissolved, removed and replaced. The tubing 1 made from commercially available metal or plastic material could also be made from the clay itself. In this application the outer surface of the tubing would have to be glazed or treated to insure that the pipe is non-porous.

Although the invention is directed to methods and materials for removing substances such as hormones, pesticides, viruses, toxins and metal salts from water supplies for home, industrial and municipal applications, this is by no means intended as a limitation thereof. The use of clay readily finds application, for example, in military and other mobile type circumstances where the only source of water is known to be contaminated to where methods of prevention of contamination of drinking sources may be required. The method also finds application in the treatment of sewage effluents from municipal treatment plants to prevent surface water contamination as well as in finishing processes for industrial wastes.

What is claimed is:

1. A method for purifying water comprising the steps of:
   contacting the water with large surface area clay particles selected from the group of natural clays consisting of attapulgite and sepiolite;
   adsorbing toxins on the clay surface; and
   separating the water from said clay containing said toxins.

2. The method of claim 1 wherein said clay comprises a colloidal grade clay.

3. The method of claim 1 wherein said surface area is at least 50 square meters/gram available surface.

4. The method of claim 1 including the step of treating the water with alum.

5. The method of claim 1 including the step of contacting said water with charcoal.

6. The method of claim 1 wherein said step of contacting said water with said large surface area clay particles comprises broadcasting said particles in powdered form over the surface of said water.

7. The method of claim 1 wherein said step of contacting said water with said large surface area clay particles comprises passing said water through a pipe containing said clay particles.

8. The method of claim 7 wherein said clay particles are coated on an inner surface of said pipe.

9. The method of claim 7 wherein the surface of said pipe is at least partially composed of the adsorbing clay.

10. The method of claim 1 wherein said step of contacting comprises percolating the water through said clay particles in granular form.

11. A method for purifying contaminated water containing toxins comprising the steps of:
   treating said water by adding a flocculating chemical to coagulate and settle at least part of said toxins from said water;
   filtering said treated water to remove a further part of said toxins;
   treating said filtered water with a chemical germicide to kill bacteria; and contacting said germicide-treated water with large surface area clay particles selected from the group of natural clays consisting of attapulgite and sepiolite to remove remaining toxins from the water.

12. The method of claim 11 wherein said clay comprises colloidal grade clays.

13. The method of claim 11 wherein said flocculating chemical is selected from the group consisting of alum and ferric sulfate.

14. A method of purifying water for human consumption comprising the steps of:

contacting the water with a flocculating chemical and large surface area clay particles selected from the group of natural clays consisting of attapulgite and sepiolite to adsorb toxins from said water;
settling said toxin-containing flocculating chemical and large surface area clay particles to remove at least part of said toxins from said water;
filtering said water to remove a further part of said toxins; and
chemically treating said filtered water to render said water safe for human consumption.

* * * * *